United States Patent [19]

Loughrey

[11] 4,157,089

[45] Jun. 5, 1979

[54] PHYSIOTHERAPY TABLE

[75] Inventor: Kevin A. Loughrey, Wishart, Australia

[73] Assignee: Janice Margaret Loughrey, Wishart, Australia

[21] Appl. No.: 860,970

[22] Filed: Dec. 15, 1977

[30] Foreign Application Priority Data

Dec. 21, 1976 [AU] Australia ............................ PC8561

[51] Int. Cl.2 ......................... A61F 5/00; A61G 13/00

[52] U.S. Cl. .......................................... 128/74; 5/62; 269/325; 108/114; 108/116

[58] Field of Search .................................. 128/70-74, 128/33; 108/111-116; 5/60, 62, 66-69; 269/322-326

[56] References Cited

U.S. PATENT DOCUMENTS

| | | | |
|---|---|---|---|
| 646,574 | 4/1900 | Gorham | 269/324 |
| 646,657 | 4/1900 | Finnegan et al. | 269/324 |
| 1,179,603 | 4/1916 | Blust | 128/70 UX |
| 1,479,522 | 1/1924 | Thorfinnsson | 128/73 |
| 2,517,681 | 8/1950 | Koerper | 128/70 |
| 3,315,667 | 4/1967 | Yoder | 128/74 |
| 3,489,142 | 1/1970 | Golay | 128/74 |
| 3,545,738 | 12/1970 | Stagg | 269/325 |

*Primary Examiner*—Robert E. Bagwill
*Attorney, Agent, or Firm*—Donald D. Jeffery

[57] ABSTRACT

A physiotherapy table for treatment of cystic fibrosis and other illnesses has a top consisting of two top sections connected hingedly end to end by adjustable joints which may be releasably locked to hold the two top sections in a number of different angular relationships, each top section being supported in individually vertically adjustable manner by an end frame to which the top section is pivoted and braced by an adjustable stay, the stays, end frames and top sections being foldable to compact form for transport.

3 Claims, 6 Drawing Figures

PHYSIOTHERAPY TABLE

BACKGROUND OF THE INVENTION

This invention relates to a physiotherapy table.

People suffering from certain illnesses including cystic fibrosis, pneumonia, bronchitis and asthma sometimes require physiotherapy for the purpose of draining their lungs of mucus. Treatment is usually carried out with the patient in a half-sitting position, or lying prone on an inclined surface or ramp, head down, and in either position being pummelled with cupped hands to cause mucus to be dislodged from the walls of the lungs. Treatment of the patient in half-sitting position allows mucus in the upper lobes of the lungs to drain into the lower lobes, and subsequent treatment in the inclined prone position allows the mucus to drain from the lower lobes into the trachea from which it is expectorated by the patient.

Commonly, this type of physiotherapy is performed on severely affected patients for approximately an hour, three times daily, and mainly at home, although hospital physiotherapy staff also perform such treatments on interned patients.

For home treatment, it is usual for a ramp to be improvised, using a flat board covered with a blanket and supported on a domestic table by chocks to bring it to the required inclination. An improvised device of this nature has the disadvantages that the patient is not likely to be supported at a height convenient and comfortable to the physiotherapist who therefore is likely to develop backache during prolonged treatment; it cannot be adjusted to serve for treatment in other positions, particularly the half-sitting position; and if the patient is taken away from home, on a visit or holiday, the device is difficult and inconvenient to transport because of its length, and facilities for setting it up may not be readily available. Furthermore, it is found that patients, after prolonged treatment prone on a ramp are likely to develop severe headaches because of blood pressure consequent in the legs being kept raised; and with steep ramp angles the patient must be restrained, normally by shoulder stops which are uncomfortable.

In hospital treatment it is also common for treatment tables to be improvised, for although multi-positional tables are available in hospitals, these are very expensive and their use can usually be justified only in special areas such as operating theatres.

The present invention has been devised with the general object of providing a physiotherapy table which overcomes the present disadvantages, being readily adjustable to suit the requirements of the patient and the physiotherapist, and which may be readily transported.

SUMMARY OF THE INVENTION

The present invention resides broadly in a physiotherapy table including a table top comprising two top sections disposed end to end; adjustable joint means interconnecting the two top sections hingedly about a transverse axis; locking means for releasably locking the two top sections in any selected one of a number of angular relationships; and supporting means supporting each of the top sections in vertically adjustable manner. Preferably the supporting means comprise end frames each hingedly connected at its top to an outer end of a table top section, having vertically adjustable legs, and having adjustable stays connected to the table top, the parts being so made and arranged that each of the end frames may be folded close to a top section, and the two top sections may be folded into parallel relationship for portability.

BRIEF DESCRIPTION OF THE DRAWINGS

In order that a preferred embodiment of the invention may be readily understood and carried into practical effect, reference is now made to the accompanying drawings, wherein.

DESCRIPTION OF THE PREFERRED EMBODIMENT

Figure 1:
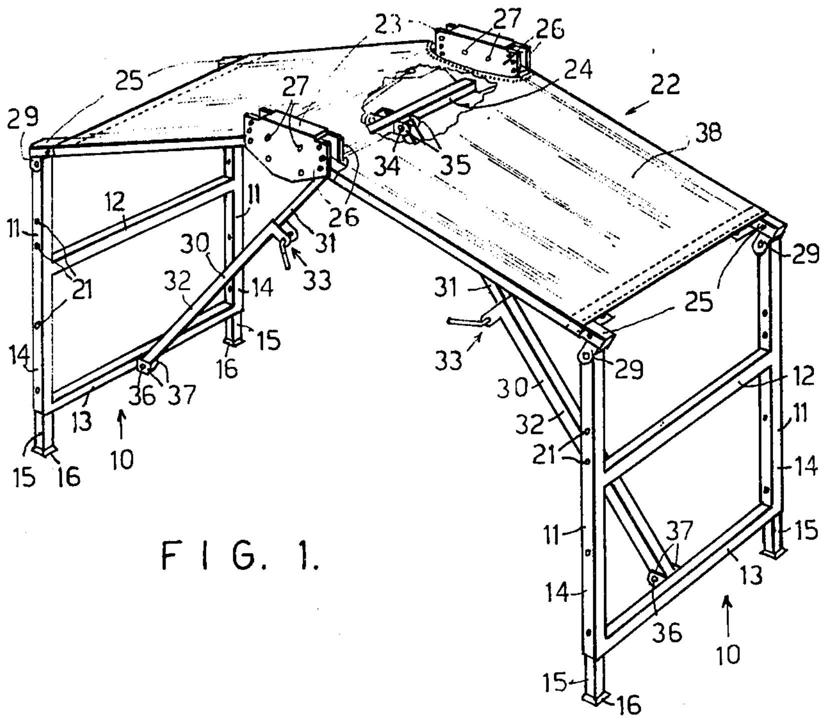
FIG. 1 is a partly broken-away perspective view of a physiotherapy table according to the invention, arranged for treatment of a patient in a prone position.

The physiotherapy table shown in the drawings includes two similar and oppositely arranged end frames 10, each having a pair of parallel telescopically adjustable legs 11 rigidly interconnected by a middle cross-piece 12 and a bottom cross-piece 13. Each of the legs consists of a square-section outer tube 14 with a square-section inner tube 15 slidable in it and having a foot 16 at its lower end, the cross-pieces 12 and 13 being welded at their ends to the two outer tubes 14 and being of similar metal tube.

Figure 4:
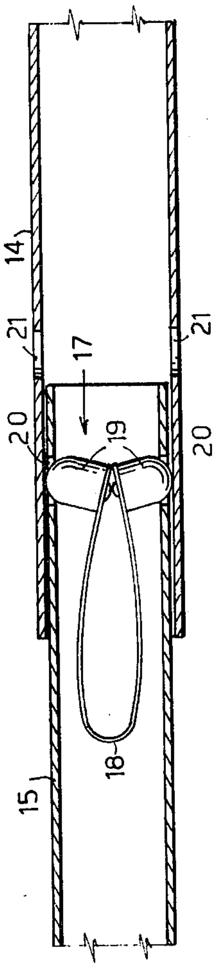
FIG. 4 is a detail sectional drawing to larger scale showing one of the several releasable catch devices of the table.

The inner tube 15 of each leg may be telescopically extended or retracted and releasably held in any selected one of a series of positions by means of a catch 17 within the inner tube and shown particularly in FIG. 4. The catch consists of a doubled-over leaf spring 18 with similar studs 19 secured to and extending outwardly in opposite directions from its extremities, these studs engaging in opposed holes 20 in the tube 15, and having rounded outer ends. When the inner tube 15 is extended or retracted to bring the studs 19 into register with any one of a number of pairs of opposed holes 21 in the outer tube 14, the studs will be forced outwardly, by the spring 18, to engage in these holes 21, locking together the two parts 14 and 15 of the leg 11. The catch may be simply released by pressing the two studs 19 in towards each other by thumb and forefinger, so the inner tube 15 may be moved slidably in the outer tube 14.

The table includes a top frame 22 consisting of two similar adjustable joint fittings 23 rigidly interconnected by a cross-piece 24, and two pairs of side members 25 which at their inner ends are pivoted to and extend from opposite ends of the adjustable joint fittings, and at their outer ends are pivoted to the tops of the legs 11 of the two end frames 10.

Each of the joint fittings 23 has two spaced parallel side plates 26 between which the inner ends of corresponding side members 25 of the two pairs are pivoted at 27. The pivots at 27 may suitably consist of spring catch devices 17 as before described and as shown in FIG. 4, and fitted in the inner end portions of the side members 25. In each of these side members 25, some distance from its inner end, is a second catch device 17 which may be selectively engaged in any one of a series of pairs of opposed holes 28 in the two side plates 26 of the adjustable joint fitting 23.

The outer ends of the side members 25 of each pair are pivoted to the upper ends of the legs 11 of an end frame 10 by the engagement of further spring catch devices 17 which are fitted in the upper ends of the outer tubes 14 of these legs and are releasably engaged in correspondingly apertured pairs of parallel lugs 29 secured to and extending from the outer end portions of the side members 25.

Two telescopically adjustable stays 30 connect the end frames 10 to the cross-piece 24 between the two joint fittings 23. Each of these stays consists of an inner tube 31 slidable in an outer tube 32 and releasably locked in desired adjustment by a clamp 33 on the outer tube. The inner tube is pivoted at 34 between a pair of parallel apertured lugs 35 secured to the middle of the cross-piece 24, and the outer tube 32 is pivoted at 36 between a pair of parallel apertured lugs 37 secured to the middle of the bottom cross-piece 13 of the end frame 10. The pivots at 34 and at 36 may consist of spring catch devices as shown at 17 in FIG. 4 and fitted in the inner and outer tubes 31 and 32 of the stay 30.

The top frame 22 of the table is provided with a cover 38 made principally of flexible sheet material which at its sides is carried down outside and under the side members 25 and is secured by an arrangement of cross-lacing through eyelets in the cover, the cover being shaped to clear the adjustable joint fittings 23.

As shown in FIG. 1, the table may be arranged with its covered top frame being in two equal sections inclining downwardly and outwardly from their junction at the joint fittings 23, the catch devices 17 of the side members 25 of the top frame being engaged in appropriate holes 28 of the side plates 26 of the adjustable joint fittings 23, and the end frames 10 being maintained upright by appropriate adjustment of the stays 30. A patient lying prone on the table so arranged may be supported at a height convenient to the physiotherapist, by extension or retraction of the legs 11. The patient, whose legs will be inclined downwards from the waist, will be far less likely to suffer from discomfort and headaches during prolonged treatment than would be the case if a single inclined surface were used. If a greater, or lesser, inclination of the patient's upper body should be required, this may be achieved by adjustment of the legs at one end or the other of the table.

Figure 2:
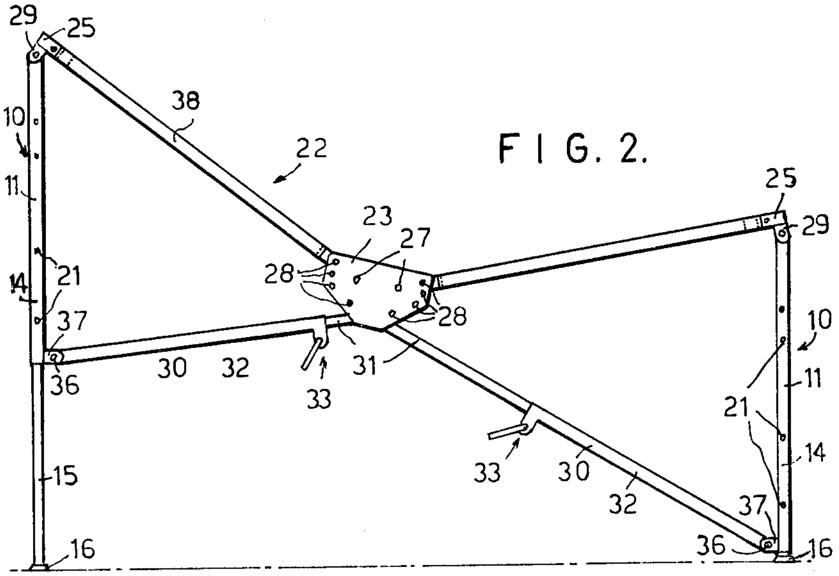
FIG. 2 is a side elevational view of the physiotherapy table adjusted for treatment of a patient in half-sitting position.

FIG. 2 shows the table arranged for treatment of a patient in half-sitting position, the two sections of the table top being locked in a different angular relationship at the adjustable joint fittings. Again, by adjustment of the lengths of the legs 11, the inclination of both the patient's upper body and lower body may be varied.

The whole of the top frame 22 may be arranged in a single plane, either horizontal or at an inclination if desired.

Figure 3:
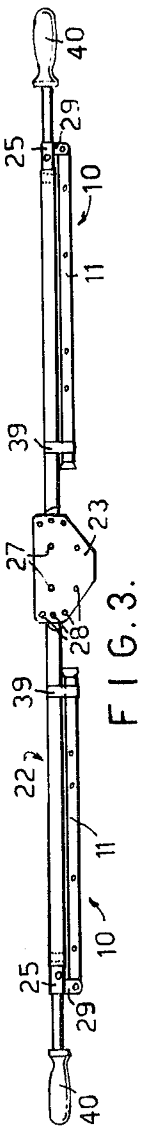
FIG. 3 is a side elevation of the table arranged for use as a stretcher.

With the two end sections of the top frame 22 locked at the joint fittings 23 in the one plane, the table may be used, as shown in FIG. 3, as a stretcher on which a patient may be carried by two persons. The stays 30 are disconnected from the lugs 35 on the cross-piece 24, are fully retracted, and are swung close to the end frames 10, which are then raised pivotally under the top frame 22 and are releasably secured in such position by any suitable means, such as holding straps at 39. Two pairs of carrying handles 40 are engaged in the outer ends of the two pairs of side members 25 of the top frame 22, and are held releasably in place by catches 17 as before described and as shown in FIG. 4.

Figure 6:
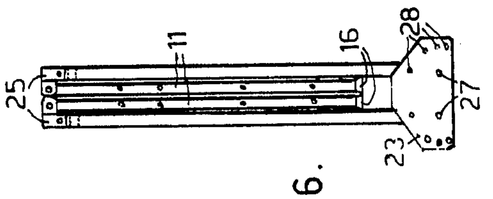
FIGS. 5 and 6 illustrate in side elevation the manner of folding the physiotherapy table for storage or transport.
Figure 5:
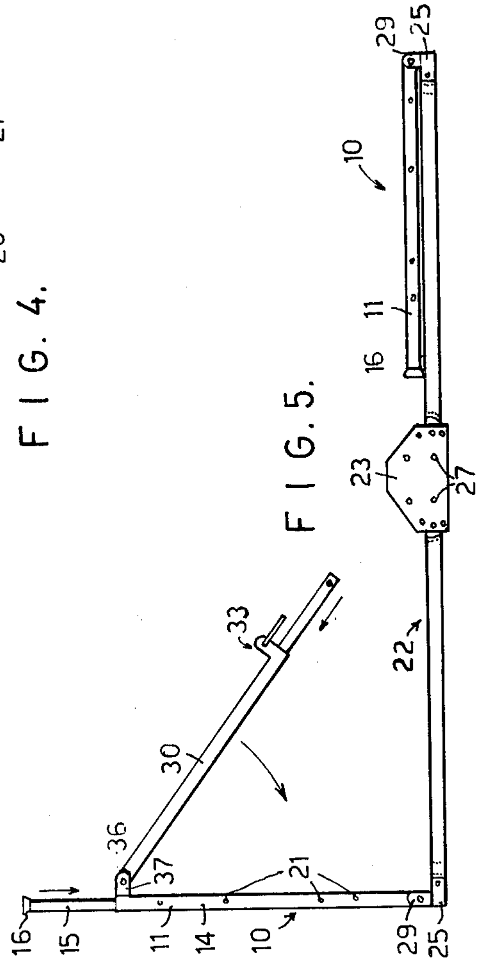

The physiotherapy table may be folded to readily portable form as shown in FIGS. 5 and 6. As shown in FIG. 5, the table is first inverted on the floor, and the stays 30 are disconnected from the lugs 35 of the cross-piece 24, are fully retracted, and are folded close to the end frames 10. The end frames, their legs 11 fully retracted, are then folded down onto the top frame 22, and finally, as shown in FIG. 6, the two pivoted sections of the top frame 22, with the end frames 10 and stays 30, are raised and brought together in a compact form.

The use of the catch devices 17 to serve as pivots as well as catches to hold interfitting parts in required relationship enables the physiotherapy table to be packaged in very compact dismantled form, the parts being capable of being quickly and easily assembled.

I claim:

1. A physiotherapy table including a table top comprising two top sections disposed end to end, adjustable hinge means connecting the two top sections for pivotal movement about a transverse axis, vertically adjustable supporting means pivotally connected to each of said top sections, and longitudinally extensible stays pivotally interconnected to and extending between said supporting means and said hinge means.

2. A physiotherapy table according to claim 1 wherein said supporting means include two end frames, each having vertically adjustable legs, and a pivotal connection between the upper part of each end frame and a top section of the table top, whereby each end frame together with an adjustable stay is pivotally foldable adjacent to the top section to which the end frame is pivoted, and the two top sections, together with the end frames and adjustable stays adjacent thereto are pivotally foldable about said adjustable hinge means to close to a substantially parallel arrangement for compact storage and carrying.

3. A physiotherapy table according to claim 1 wherein said adjustable hinge means comprises, at each side of said table, spaced parallel side plates which receive side members of said top sections, said side plates being formed with a series of aligned openings into which a catch device carried by said associated side member can resiliently extend for retaining the same in the desired adjusted position, and a cross member extending between said side plates, said stays being pivotally secured to said cross member.

* * * * *